United States Patent [19]
Dorr et al.

[11] Patent Number: 5,985,302
[45] Date of Patent: Nov. 16, 1999

[54] METHOD FOR DEACTIVATING A CONTAMINANT

[75] Inventors: Robert T. Dorr; David S. Alberts, both of Tucson, Ariz.

[73] Assignee: Supergen, Inc., San Ramon, Calif.

[21] Appl. No.: 09/113,734

[22] Filed: Jul. 10, 1998

Related U.S. Application Data

[62] Division of application No. 07/973,211, Nov. 6, 1992, Pat. No. 5,811,113, which is a continuation of application No. 07/788,157, Nov. 6, 1991, abandoned, which is a continuation-in-part of application No. 07/715,722, Jun. 14, 1991, abandoned, which is a continuation of application No. 07/377,062, Jul. 10, 1989, abandoned, which is a continuation-in-part of application No. 07/344,213, Apr. 27, 1989, abandoned.

[51] Int. Cl.⁶ .......................... A01N 25/34; A01N 25/00; D06L 3/00
[52] U.S. Cl. .......................... 424/404; 424/405; 424/407; 424/661; 8/108.1; 8/137; 252/187.24; 252/187.25; 252/187.26; 252/187.27; 252/187.28; 206/812
[58] Field of Search ..................... 424/404, 405, 424/407, 661; 8/108.1, 137; 252/187.24, 187.25, 187.26, 187.27, 187.28; 206/812

[56] References Cited

U.S. PATENT DOCUMENTS

| | | | |
|---|---|---|---|
| 4,594,239 | 6/1986 | Pluim | 424/10 |
| 4,814,335 | 3/1989 | Kim | 514/257 |
| 4,976,921 | 12/1990 | Itagaki | 422/28 |
| 4,998,984 | 3/1991 | McClendon | 206/205 |
| 5,006,339 | 4/1991 | Badgery | 424/404 |
| 5,087,450 | 2/1992 | Lister | 424/402 |

*Primary Examiner*—Gollamudi S. Kishore
*Attorney, Agent, or Firm*—Cahill, Sutton & Thomas, P.L.C.

[57] ABSTRACT

Methods, compositions and a kit for deactivating spills or leaks of HIV infected blood or anticancer drugs by applying to the leak or spill an aqueous solution containing calcium hypochlorite or sodium hypochlorite as the active ingredient. In order to thicken the aqueous solution and thus keep it from spreading beyond its intended area of application, the solution of calcium hypochlorite contains methylcellulose. In addition to chemically deactivating the active anticancer drug, the solution of the invention also effectively decolorizes it, thus preventing permanent stains on any surface or fabric with which the anticancer drug comes into contact.

4 Claims, No Drawings

METHOD FOR DEACTIVATING A CONTAMINANT

CROSS-REFERENCE TO RELATED APPLICATION

This application is a divisional, pursuant to 37 C.F.R. §1.53(b), of parent application Ser. No. 07/973,211, filed on Nov. 6, 1992 and entitled "METHOD AND COMPOSITION FOR DEACTIVATING HIV INFECTED BLOOD AND FOR DEACTIVATING AND DECOLORIZING ANTICANCER DRUGS", now U.S. Pat. No. 5,811,113, which is a continuation of application Ser. No 07/788,157, filed on Nov. 6, 1991 (now abandoned), which is a continuation-in-part of application Ser. No. 07/715,722, filed on Jun. 14, 1991 (now abandoned), which is a continuation of application Ser. No. 07/377,062, filed Jul. 10, 1989, now abandoned, which is a continuation-in-part of application Ser. No. 07/344,213, filed on Apr. 27, 1989 now abandoned, and the benefit of such earlier filing dates is hereby asserted pursuant to 35 U.S.C. §120.

BACKGROUND OF THE INVENTION

This invention relates to methods and compositions for deactivating HIV (human immunodeficiency virus) infected blood and anticancer drugs which may have been accidentally spilled or which have leaked from a patient, thus constituting a possible hazard to attending personnel. In addition, some anticancer drugs are inherently colored and such leakages or spills may stain clothes. The invention is effective to eliminate such stains by decolorizing the drug.

Among the known antineoplastic or anticancer drugs which are used for treating cancers of various types, some are known or suspected to be in themselves carcinogenic. In addition, some of these anticancer drugs are also dyes capable of creating unsightly stains on clothes and other fabrics such as bedsheets. Accordingly, when solutions of anticancer drugs are spilled or leaked, a possible hazard to attending personnel, as well as an unsightly stain on clothing and the like, may be created.

BRIEF DESCRIPTION OF THE INVENTION

In accordance with the invention, spills or leaks of HIV infected blood and/or anticancer drugs are chemically deactivated by applying to the leak or spill an aqueous solution containing sodium or calcium hypochlorite as the active ingredient. In one embodiment, in order to thicken the aqueous solution and thus keep it from spreading beyond its intended area of application, the hypochlorite solution contains methylcellulose. In addition to chemically deactivating the active anticancer drug, the composition of the invention also effectively decolorizes it, thus preventing permanent stains on any surface or fabric with which the anticancer drug comes into contact.

In a second embodiment of the present invention, spills or leaks of HIV infected blood and/or anticancer drugs on stainless steel or ceramic work surfaces vulnerable to etching by the corrosive alkaline sodium or calcium hypochlorite solutions are inactivated with a two-step, towelette swabbing kit and process. A first absorbent, fibrous (preferably cotton and/or synthetic blend) towelette, impregnated with calcium hypochlorite or, preferably, sodium hypochlorite, is swabbed over the spilled HIV infected blood- or drug-containing work surface to deactivate the spilled compound. A second absorbent, fibrous (preferably cotton and/or synthetic blend) towelette, impregnated with sodium thiosulfate, is then swabbed over the spilled HIV infected blood- or drug-containing work surface to neutralize the alkaline calcium or sodium hypochlorite residue from the first towlette, so as to prevent the alkaline residue from corroding or etching the work surface.

DETAILED DESCRIPTION OF THE PREFERRED EMBODIMENTS

In accordance with the invention, HIV infected blood, or any of a number of active anticancer drugs, can be inactivated by applying thereto an aqueous solution containing 4–40% by weight of calcium or sodium hypochlorite. HIV infected blood, as well as any anticancer agent which can undergo oxidative or alkaline degradation can be deactivated in accordance with the method of the invention. Among the anticancer agents which can be effectively deactivated are the following:

anthracyclines, such as doxorubicin, daunorubicin, and epirubicin anthracenes, such as mitoxantrone and bisantrene alkylating agents, such as mitomycin-c, melphalan, cyclophosphamide, ifosphamide, thio-TEPA, decarbazine, carmustine, cisplatin, and carboplatin antimetabolites, such as fluorouracil, cytarabine, methotrexate, and mercaptopurine biologicals, such as α-interferon, interleukin 2, tumor necrosis factor, G-CSF, and GM-CSF miscellaneous compounds, such as vincristine, vinblastine, actinomycin D, bleomycin, etoposide, L-asparaginase, mAMSA, vindesine, and teniposide In addition to chemically deactivating the anti-cancer drugs, the method of the invention is also effective to decolorize those, e.g., the anthracyclines, doxorubicin and daunorubicin, which are naturally red in color, and the alkylating agent mitomycin C, which is naturally purple in color, which stain fabrics which they contact. The method of the invention renders the naturally colored anticancer drugs colorless, thus preventing permanent damage to clothes or other materials which come in contact with the drugs. It has been found that deactivation and colorization of the anti-cancer drug occur within approximately 30–60 seconds after a suitable solution of hypochlorite is applied in accordance with the invention.

The hypochlorite solution can be applied in any convenient manner, suitably by means of a manually operated spray bottle or other mechanical spray device. It is also within the contemplation of the invention to use, in addition to such mechanical devices, an aerosol dispenser activated by a conventional aerosol propellant.

If the HIV infected blood and/or the drugs are spilled on a ceramic or stainless steel work surface, which surfaces may be vulnerable to permanent etching or disfiguration by the alkaline deactivator compounds calcium hypochlorite and sodium hypochlorite, it is preferred to use a two step, towelette swabbing kit and procedure to deactivate the spilled material. A first absorbent, fibrous (preferably cotton and/or synthetic blend) towelette is impregnated with an aqueous solution containing 4–40%, but preferably less than 6%, of a deactivator compound such as calcium hypochlorite or, preferably, sodium hypochlorite by applying to the first towelette an excess of aqueous deactivator solution, beyond that amount necessary to completely saturate the first towelette. The ratio of deactivator volume to towlette weight should be in the range of about 1.8 to 15 ml deactivator per gram towlette (preferably 6.5 to 15 ml/gm); alternatively, the ratio of deactivator volume to towlette surface area should be in the range of about 0.01 to 0.2 ml deactivator per cm² of towlette. The deactivator-impregnated towlette is wiped or swabbed over the spilled HIV infected blood- or drug-containing work surface to deactivate the spilled compound; if the spilled compound is a drug which creates a stain, deactivation is indicated by disappearance of the stain after swabbing.

A second absorbent, fibrous (preferably cotton and/or synthetic blend) towlette, impregnated with an aqueous solution of 4–40%, but preferably less than 6%, of sodium thiosulfate, by applying to the second towlette an excess of the aqueous sodium thiosulfate solution, beyond that amount necessary to completely saturate the second towlette. The ratio of sodium thiosulfate volume to towlette weight should be in the range of about 1.8 to 15 ml deactivator per gram towlette (preferably 6.5 to 15 ml/gm); alternatively, the ratio of sodium thiosulfate volume to towlette surface area should be in the range of about 0.01 to 0.2 ml deactivator per cm² of towlette. The sodium thiosulfate-impregnated towlette is then wiped or swabbed over the spilled HIV infected blood- or drug-containing work surface to neutralize the alkaline calcium or sodium hypochlorite residue from the first towlette, so as to prevent the alkaline residue from corroding or etching the work surface. Furthermore, sodium thiosulfate itself is capable of deactivating several carcinogenic anti-cancer drugs, such as the alkylating agents nitrogen mustard and cisplatin.

Suitable towlettes include "Terri® Wipers", nylon-reinforced 4 ply, #34770, each measuring 17×23 cm and weighing approximately 2.6 gram, manufactured by Kimat room temperature for 10 days. The strips were then removed from the vials, air dried, and weighed. To test the deactivation ability of the sodium hypochlorite solution remaining in each vial, 0.1 ml of a solution containing 1.0 mg/ml of the drug doxorubicin was applied to each of several "Terri® Wipers", nylon-reinforced 4 ply, #34770, each measuring 17×23 cm and weighing approximately 2.6 gram, manufactured by Kimberly Clark, Neenah, Wis. 0.1 ml samples of the sodium hypochlorite solution remaining in each vial were then added to a respective doxorubicin-containing Terri® Wiper. Deactivation was inferred by a color change from red to colorless.

The results of the "Texwipe®" tests are summarized in table A. Of the four "Texwipe®" towlettes tested, Technicon A yielded the best results, although the bleach was completely inactivated by the Technicon fabric after seven weeks. Two of the towlettes (Absorbanal Applicators and TX801 Applicators) exhibited significant weight gain after storage in the bleach, indicating possible covalent bonding of the hypochlorite directly to the fabric. The results for those three towlettes suggest that it may be preferable to add excess solution to the towlettes to assure adequate deactivating activity after storage. A fourth "Texwipe®" towlette (TX811) was completely dissolved by the bleach, and is thus not suitable for this application. Preferably, the sodium hypochlorite and sodium thiosulfate impregnated towlettes are prepared in advance and stored in separate sealed foil packages or the like until use.

TABLE A

TEXWIPE SAMPLE TESTS: Compatibility with Sodium Hypochlorite

| Sample A | No. | Weights (g) | Quality | Appearance | Activity with respect to Doxorubicin | Dry Weight | % Difference In Weight |
|---|---|---|---|---|---|---|---|
| Technicon A | 1) | .0674 | Paper-like texture; Tears easily | Clear solution | Inactive | .0619 | +8 |
|  | 2) | .0462 |  |  |  | .0472 | +2 |
|  | 3) | .0501 |  |  |  | .0460 | −9/2 |
|  |  |  |  |  |  | Average | +0.6 |
| Absorbanal Applicator B | 1) | .420 | Thick, soft; Tears with difficulty | Yellow solution | Highly active | .1025 | +144 |
|  | 2) | .511 |  |  |  | .1238 | +142 |
|  | 3) | .544 |  |  |  | .1234 | +123 |
|  |  |  |  |  |  | Average | +118 |
| TX811 Applicator D | 1) | .0266 | Paper-like quality; very thin | Clear solution | Slowly active; Incomplete inactivation; No wipes left | None Available |  |
|  | 2) | .0966 |  |  |  |  |  |
|  | 3) | .0286 |  |  |  |  |  |
| TX801 Applicator D | 1) | .1128 | Soft-life but sturdy | Yellow solution | Highly active | .1901 | +88 |
|  | 2) | .0966 |  |  |  | .1582 | +64 |
|  | 3) | .1031 |  |  |  | .1733 | +68 |
|  |  |  |  |  |  | Average | +67 |

Bleach: National Sanitary Supply 5.25% w/v Sodium Hypochlorite
*All white cloth, single thickness; Approximate sample size 1 × 1 inch.

berly Clark, Neenah, Wis., in addition to the the following "Texwipe®" towlettes, manufactured by Texwipe Corporation, Upper Saddle River, N.J.: Technicon A, Absorbanal Applicators, and TX801 Applicators.

The compatability of the various "Texwipe®" towlettes with sodium hypochlorite was tested using the following procedure. Strips of the different Texwipe® fabrics were cut into 1×1 inch squares and weighed. The fabric strips were then placed in 15 ml plastic vials. 5 ml of an aqueous solution containing 5.25% by weight of sodium hypochlorite was added to each vial. The vials were capped and incubated It has also been determined that HIV infected blood and most anticancer drugs can be deactivated by application of a solution of calcium or sodium hypochlorite in water at a concentration of 4% by weight. A few of the anticancer drugs, notably mitoxantrone, may require the use of a solution having a substantially higher concentration of hypochlorite, up to 40% by weight, in order to achieve substantially complete deactivation of the anticancer drug.

In order to maintain the hypochlorite solution in contact with the drug, and to avoid displacement, it is desirable to increase the viscosity of the solution of hypochlorite. It has been found, however, that conventional thickeners tend to deactivate the solution of hypochlorite at different rates. Thus, gelatin causes an immediate violent endothermic reaction when added to a solution of calcium hypochlorite, while polyvinylpyrolidine and polyethylene glycol cause deactivation of the hypochlorite solution within one hour. Methyl cellulose deactivates the hypochlorite, but at relatively slow rates so that hypochlorite-methylcellulose solutions maintain a practical degree of effectiveness for a reasonable time (e.g., 8 hours) after mixing.

In addition to deactivating of the hypochlorite, addition of a thickener to a solution of hypochlorite causes an interaction between the hypochlorite and the thickener which reduces the ability of the thickener to increase the viscosity of the solution. Thus, for example, the viscosity of a typical solution of calcium hypochlorite and methylcellulose drops by more than two-thirds after a period of three days.

While the deactivating ability of the hypochlorite and the thickening ability of the thickeners decrease most rapidly in aqueous solution, similar effects occur when mixtures of the dry powders are stored. It has been found that mixtures of calcium hypochlorite and methylcellulose powders stored in a dry condition lose a significant proportion of deactivating ability within 5 days and became almost completely inactive after 30 days at room temperatures, such that complete inactivation can occur after 10 days at 50° C.

From the above, it is apparent that mixtures of hypochlorite and thickener, whether in solution or in dry form, have very limited shelf lives. The solutions of the invention should be prepared fresh immediately before use and should not be stored for any extended periods of time. Accordingly, the invention is suitably prepared and utilized as a two-package system including a first package containing an appropriate quantity of the hypochlorite, and a second package containing an appropriate quantity of the hypochlorite, and a second package containing an appropriate quantity of the thickener, the contents of the package to be dissolved in a predetermined volume of water immediately before use. In order to maintain the appropriate concentrations of hypochlorite and thickener in the finished solution, i.e., 4–40% by weight of hypochlorite and 1–5% by weight of thickener, the proportion by weight of hypochlorite in the first package to the weight of thickener in the second package is in the range of 1:1 to 40:1, and preferably 1.2:1 to 2.0:1.

Methylcellulose maintains its ability to thicken the deactivating solutions of the invention for relatively long periods of time with a relatively small effect on the deactivating ability of the hypochlorite. Accordingly, methylcellulose is the preferred thickener for use in the invention. Other common thickeners, such as agar, polyvinylpyrolidine, polyethylene glycol, and gelatin, either react violently when mixed with the hypochlorite or produce solutions having too short an effective life (minutes to hours) for practical use.

The effectiveness of the method and composition of the invention are demonstrated in the following examples.

EXAMPLE 1

Mutagenic Activity

Solutions of DNA intercalators (doxorubicin, daunorubicin and mitoxantrone) in concentrations of 10 ng/ml D5W were applied in 5 ml quantities to separate petri dishes. Two different concentrations of calcium hypochlorite, 40 g/l and 423 g/l, were applied in 1 ml. volumes separately to the anticancer drug solutions in each petri dish for a period of one minute. After thorough mixing and neutralization of the pH to 7.4 using HCl, 1 ml of each petri dish solution was applied to 35 mm petri dishes containing cultures of Salmonella Typhimurium TA 98 strain. The petri dishes containing bacteria plus overlaid mixtures of calcium hypochlorite/anticancer drug and control plates with bacteria alone were then incubated at 37° C. for 24 hours. The colonies of revertant organisms were counted and reported in Table 1.

TABLE 1

Mutagenic Activity from DNA Intercalators Treated with Calcium Hypochlorite

| DNA Intercalator | No. Colonies of Revertant Organisms Calcium Hypochlorite Concentration | | |
|---|---|---|---|
| (10 ng/ml | None | 40 g/l | 423 g/l |
| Doxorubicin | 257 | 0 | 0 |
| Daunorubicin | 365 | 0 | 0 |
| Mitoxantrone | 164 | 44 | 0 |
| None (control) | 20 | 0 | 0 |

Table 1 reports the number of colonies of revertant (mutated) bacterial organisms resulting from calcium hypochlorite treatment at two different concentrations of three different anticancer drugs. The control bacterial plates (i.e., untreated with anticancer drug or calcium hypochlorite) contained only 20 bacterial colonies after 24 hours. On the other hand, the bacterial plates treated with the anticancer drug in the absence of calcium hypochlorite contained between 164 and 365 bacterial colonies per plate. At the higher concentration of calcium hypochlorite there were no colonies of revertant organisms in the bacterial plates and at the lower concentration of calcium hypochlorite only mitoxantrone was associated with bacterial revertant growth.

EXAMPLE 2

Anthracene or Anthracycline Chromophore Recovery by High Performance Liquid Chromatography Treatment of the drugs with calcium hypochlorite was carried out as described in Example 1. One ml aliquots of doxorubicin, daunorubicin and mitoxantrone, separately, were taken from the petri dishes after calcium hypochlorite exposure at two different concentrations for a period of one minute. Ten (10) ng of each of the anticancer drug (based on the final concentration resulting from the addition of calcium hypochlorite to the separate petri dishes containing each anticancer agent) was added to a high performance liquid chromatography column and standard HPLC assays were carried out. A reverse phase C-18 bonded phase HPLC procedure was used. The mobile phase consisted of 30:70 $CH_3CN$:ammonium acetate at a flow rate of 2 ml/min., using a Varian model 5020 HPLC unit. The anticancer drugs were detected using excitation at 480 nm and emission at 550 nm with a Schoeffel model FS 970 fluoroescence detector. At the higher concentration of calcium hypochlorite (423 g/l) the treatment resulted in complete chemical degradation of all three anticancer drugs. At the lower concentration, there was no chemical evidence of either doxorubicin or daunorubicin and approximately 60% degradation of mitoxantrone.

TABLE II

Anthracene or Anthracycline Chromophore Recovery
by High Performance Liquid Chromatography

| DNA Intercalator | Concentration ng by Fluroescence* Calcium Hypochlorite Concentration | | |
|---|---|---|---|
| (10 ng on Column) | 0-(Control) | 40 g/l | 423 g/l |
| Doxorubicin | 9.7 | 0 | 0 |
| Daunomycin | 9.8 | 0 | 0 |
| Mitoxantrone | 10.1 | 3.8 | 0 |

*Reverse phase C-18 bonded phase, mobile phase of 30:70 $CH_3CN$: ammonium acetate, flow rate 2 ml/min, (Varian Model 5020); detection using excitation at 480 nm and emission at 550 nm (Schoeffel Model FS 970)

EXAMPLE 3

Compatibility of Hypochlorite and Methylcellulose in Aqueous Solution

The compatibility of calcium hypochlorite with methylcellulose in aqueous solution was investigated in a series of tests. Freshly made solutions containing 4% by weight of calcium hypochlorite and 2.5% by weight of methylcellulose were examined for viscosity, pH, and ability to deactivate anticancer drugs. Measurements of pH were made by a commercial pH meter while viscosity was measured by an instrument using the falling ball method. The ability to inactivate anticancer drugs was evaluated by titration of stock solutions of doxorubicin (2 mg/ml) and mitoxantrone (2 mg/ml). The tests were performed by titrating the inactivating solution onto absorbent paper containing measured amounts of each anticancer agent. The end point was the number of drops of inactivating solution required for complete neutralization of the red color of doxorubicin or the blue color of mitoxantrone.

The viscosity, pH, and neutralizing ability of the solutions were measured at intervals over a period of three to four days. The freshly made mixture had an initial viscosity of 32 cps, a pH of 11.0, and an assigned value of 100% inactivating activity. These values changed rapidly after the solution was prepared. The viscosity dropped by almost 40% in the first 12 hours, and by 68% within 72 hours, the pH value dropped to 7.0 in one day, and the inactivating activity dropped to 50% within a period of 12–48 hours, depending on how thoroughly the solid ingredients were dissolved in the mixture. Those compositions in which the components were not thoroughly dissolved retained inactivating activity for longer periods of time. By contrast, solutions in which the hypochlorite and methylcellulose were thoroughly dissolved became more inactive at a faster rate. In general, a loss of 10–20% of activity occurred within 8 hours after the aqueous solution was prepared. Accordingly, provided the solution was used within 8 hours of preparation, most of the inactivating ability of the solution was retained.

EXAMPLE 4

Stability of Dry Mixtures of Calcium Hypochlorite and Methylcellulose

The stability of mixtures of calcium hypochlorite and methylcellulose in dry form was tested by preparing individual mixtures of 4 grams of calcium hypochlorite and 2.5 grams of methylcellulose, and storing the mixtures in plastic bottles at room temperature (25° C.) and at elevated temperature (50° C.). At various times, water was added to the mixture of dry ingredients in an amount sufficient to produce 100 ml. of a solution containing 4 grams of calcium hypochlorite and 2.5 grams of methylcellulose. The solution was examined for pH, viscosity, and inactivating activity as described above. The results are given in Table III.

TABLE III

Stability of Calcium Hypochlorite and Methylcellulose Powders

| | | Properties of Solution** | | |
|---|---|---|---|---|
| Days of Storage | Temperature °C.) | pH | Viscosity (cps) | Inactivating Activity* |
| 1 | 25 | 11 | 30 | 100 |
| 5 | 25 | 10.5 | 28 | 85 |
| 7 | 25 | 10 | 27 | 71 |
| 10 | 25 | 8.5 | 18 | 60 |
| 14 | 25 | 7.0 | 5.7 | 45 |
| 21 | 25 | 6.4 | 4 | 20 |
| 30 | 25 | 6.1 | 2.5 | 8 |
| 1 | 50 | 11 | 30 | 97 |
| 5 | 50 | 9 | 12 | 40 |
| 7 | 50 | 7.5 | 3 | 10 |
| 10 | 50 | 6.0 | 1 | 0 |

*Determined by titration to color neutralilty for stock solutions of doxorubicin and mitoxantrone (1 mg/ml each). Results standardized to initial activity.
**100 ml of solution containing 4 g of calcium hypochlorite and 2.5 g of methylcellulose.

The data of Table III show that significant activity was lost after only five days of storage of the dry ingredients and that the mixture had become almost completely inactive after storage for 30 days at room temperature or 10 days at 50° C. It is apparent, therefore, that even when mixed as dry powders, the active ingredients of the mixture inactivate each other in a manner which is dependent on time and temperature.

EXAMPLE 5

Stability of Mixtures of Hypochlorite and Other Thickeners in Aqueous Solution

In addition to methylcellulose, four common viscosity enhancing agents were tested for suitability for increasing the viscosity of hypochlorite solutions. The results of these tests are reported in Table IV. It will be seen that, except for methlycellulose, the other thickeners were unsuitable for use in calcium hypochlorite solutions either because they became quickly deactivated (polyvinylpyrolidine and polyethylene glycol) or caused a violent reaction (agar, gelatin). Agar reacted violently and caused the solutions to thicken to a gel.

TABLE IV

Tests of Pharmaceutical Thickeners in Calcium
Hypochlorite Solutions (4 g Ca(OCl)$_2$ per 100 mL)

| Stiffening Agent | g/100 mL | Viscosity (cps)* | Time to Loss of Inactivating Ability Mitoxantrone | Doxorubicin |
|---|---|---|---|---|
| Polyvinylpyrolidine | | | | |
| 40,000 Molecular Weight | 14 | 17.8 | 30 min. | 1 hr. |
| Polyethylene Glycol Mixture | | | | |
| 3,350 Ave. Molec. Wt. | 30 | 18 | 30 min. | 1 hr. |
| 400 Ave. Molec. Wt. | 30 | | | |
| Agar** | | | | |
| (Vigorous exothermic | 2.5 | Too thick to evaluate | 24 hr. | 24 hr. |
| reaction upon mixing, | | | | |
| forming a gel) | 5.0 | Too thick to evaluate | 48 hr. | 48 hr. |
| | 10.0 | Too thick to evaluate | — | — |
| Gelatin | 1 | Impossible to evaluate due to an immediate violent endothermic reaction. | | |
| | 2.5 | | | |
| | 10 | | | |

*Measured immediately after mixing using the falling ball method.
**The exothermic reaction precludes the use of agar in clinical settings because of potential explosive properties.

EXAMPLE 6

HIV Inactivation by Dilute Calcium Hypochlorite

The ability of dilute calcium hypochlorite to inactivate HIV was tested against an HIV-infected CD4+ human cell line (H9/IIIB). A saturated solution of dilute calcium hypochlorite completely inactivated infected human T-lymphocytes.

Procedure:

H9/IIIB cells (10$^6$ cells/ml of complete culture medium, RPMI in 10% fetal calf serum [FCS]) were exposed to an aqueous solution containing 4% by weight of calcium hypochlorite for 15 minutes; the volumetric ratio of culture medium to calcium hypochlorite solution was 1:1, or a 50% dilution of a 4% dilute calcium hypochlorite solution in culture medium containing 10% serum. The cells were subsequently washed three times with 10% FCS RPMI and plated in fresh medium and allowed to incubate at 37° C. for three days, to allow any residual live virus and/or virus-infected cells to develop after the brief exposure to the dilute calcium hypochlorite solution. The cells were again pelleted and exposed to lytic CD4+ human cell line (MOT) as a target for any viable virus. The target MOT cells will lyse when infected with HIV. These cells were then allowed to incubate an additional four days. Next, the cells were incubated with human anti-HIV antibody (prepared in accordance the the procedures described in Lake DA, Sugano T, Matsumoto Y, et al: "A Hybridoma Producing Monoclonal Antibody Specific for Glycoprotein 120 kDa of Human Immunodeficiency Virus (HIV-1), Life Sciences 45:iii-x, 1989.) for one hour, and then washed and incubated with fluorescent labeled goat anti-human IgG for one hour. The method for HIV detection by formaldehyde fixation and flow cytometry was in accordance with the method described in Lifson JD, Sasaki DT, Engleman EG: "Utility of Formaldehyde Fixation for Flow Cytometry and Inactivation of the AIDS Associated Retrovirus", J Immunological Methods 86:143–149, 1986.

Controls:

As a positive control, the above procedure was followed with HIV-infected H9/IIIB cells exposed only to culture medium rather than to culture medium and calcium hypochlorite. As a negative control, the above procedure was followed with uninfected H9 cells exposed to an aqueous solution containing 4% by weight of calcium hypochlorite.

Results:

After a four day incubation period, the HRV positive control cultures exhibited large concentrations of swollen, HIV-infected MOT cells. The calcium hypochlorite solution (n=4 each) completely lysed non-infected as well as HIV infected MOT cells, and there were no viable HIV varions present.

HIV infected cells exposed to dilute calcium hypochlorite were also viewed under a fluorescent microscope following exposure to the fluorescent anti-HIV antibody. They showed no signs of HIV infection and were identical to the negative control.

Conclusion:

Dilute calcium hypochlorite completely inactivates human immunodeficiency virus when added to infected cell cultures in a 1:1 volumetric ratio. The cells are completely lysed by dilute calcium hypochlorite and no HIV antibody binding is detectable using a goat antibody specific to the 120 kDa viral glycoprotein.

EXAMPLE 7

HIV Inactivation by Dilute Calcium Hypochlorite Containing a Thickener

The materials and methods of Example 6 were repeated, except that the aqueous bleach solution applied to the infected and uninfected H9 cells included 2.5% by weight of the thickener methlycellulose in addition to 4% by weight of calcium hypochlorite. The results were the same as those obtained in Example 6. The MOT cells were lysed and the residual material was not infectious; however, the fluorescent entibody technique could not be completed because of the methlycellulose thickening effect.

EXAMPLE 8

Use of Towlette Swabs for Deactivating Anticancer Drug Materials

Experimental Materials

Test Swabs: 17×23 cm nylon-reinforced 4 ply, #34770, each weighing approximately 2.6 gram Terri® Wipers, manufactured by Kimberly Clark, Neenah, Wis.

Bleach: 5.25% by weight aqueous solution of household bleach, i.e., sodium hypochlorite ($NaHClO_4$), supplied by National Sanitary Supply, Los Angeles, Calif., having a pH of approximately 11.2.

Sodium thiosulfate: 5% by weight aqueous solution, supplied by Tarijian Labs, Inc., Queens Village, N.Y.

Doxorubicin: 1 mg/ml aqueous solution, supplied by Adria Labs, Columbus, Ohio.

Experimental Procedure 0.1 ml of the doxorubicin solution (1 mg/ml) was applied onto a fresh, dry towelette. The doxorubicin solution caused a red colored stain to appear on the surface of the towelette. One drop of the household bleach solution was then soueezed onto the red stained, doxorubicin contaminated towelette surface. Within 10–15 seconds the red color disappeared, indicating that the bleach solution had chemically inactivated the doxorubicin. The pH of the bleach solution on the surface of the towlette was found to be 11.2, as determined by a pH meter.

In a glass container, 10 ml of the 5% sodium thiosulfate solution was added to 10 ml of the 5.25% bleach solution; a slight exothermic reaction resulted from the addition of the sodium thiosulfate to the bleach solution. Between 10–20 drops of the resulting mixture was then added to a second doxorubicin stain on a towelette. The red doxorubicin stain remained on the towlette, indicating that the sodium thiosulfate neutralized the bleach solution so that the bleach could no longer inactivate the doxorubicin on the towelette. A pH meter was again used to determine the pH (1.3) of the combined sodium thiosulfate-bleach mixture on the surface of the towlette.

These results indicate that household bleach used in low volume can cause the chemical inactivation of doxorubicin droplet contamination on a paper towelettLe. Mixing together ecrual volumes of the 5% sodium thiosulfate solution and the 5.25% household bleach solution results in a mixture incapable of decolorizing the doxorubicin contamination on the dry towelette, indicating that the sodium thiosulfate neutralized the oxidizing action of the household bleach. The pH of the combination sodium thiosulfate/household bleach solution was 1.3.

Sodium thiosulfate increases the carcinogen inactivating capacity of the sodium hypochlorite solution due to the thiosulfate's ability to bind chemically to various alkylating type molecules such as nitrogen mustard and cisplatin. Furthermore, the addition of sodium thiosulfate to the sodium hypochlorite solution prevents permanent etching of stainless and ceramic surfaces caused by the alkaline sodium hypochlorite solution.

Various combinations and pHs of acid alcohol (a mixture of absolute ethanol and 0.1 N hydrochloric acid), mixed with sodium hypochlorite and/or sodium thiosulfate, were evaluated as listed below.

In a series of experiments, between 1–10 ml acid alcohol, having pHs in the range of between 1–3.75, were added to between 5–10 ml household bleach. The acid alcohol was unable to inactivate the household bleach until the ratio of acid alcohol to bleach (having a pH of 1.0) was 2:1; at that high ratio of acid alcohol to bleach, a moderate exothermic reaction as well as noxious fumes occurred.

In another series of experiments, between 2.5–10 ml sodium thiosulfate, 5–10% were added to between 0–9 ml ethanol, together with 10 ml household bleach. The mixture of the three chemicals resulted in moderately severe exothermic reactions and inactivation of bleach's oxidizing activity only when equal ratios of 5% sodium thiosulfate were added to the bleach (in the presence of ethanol), and the resulting pH was below 2.

The foregoing description has been given for clearness of understanding only, and no unnecessary limitations should be understood therefrom, as modifications will be obvious to those skilled in the art.

EXAMPLE 9

Use of Towlette Swabs for Deactivating Work Surfaces Contaminated by An Anticancer Drug Material The Experimental Materials used are as described above in Example 8. A first fresh, dry test swab or towlette is impregnated with a 5.25% by weight aqueous solution of sodium hypochlorite by applying 5 (five) ml. of the sodium hypochlorite solution to the test swab. A second fresh, dry test swab or towelette is impregnated with a 5% by weight aqueous solution of sodium thiosulfate by applying 5 (five) ml. of the sodium thiosulfate solution to the test swab.

Doxorubicin is placed on a stainless steel work surface, which should cause a red stain to appear. The sodium hypochlorite impregnated towlette is then wiped or swabbed, over the doxorubicin spill, which should cause the red stain to disappear, indicating chemical inactivation of the doxorubicin by the sodium hypochlorite.

The sodium thiosulfate impregnated towlette is then wiped, or swabbed, over the work surface containing the chemically inactivated doxorubicin spill. The sodium thiosulfate should neutralize any residual sodium hypochlorite left on the work surface, thereby preventing the stainless steel surface from being etched by the residual alkaline sodium hypochlorite solution.

EXAMPLE 10

Use of Towlette Swabs for Deactivating Work Surfaces Contaminated bv HIV Infected Cells Experimental Materials Test Swabs: 17×23 cm nylon-reinforced 4 ply, #34770, each weighing approximately 2.6 gram Terri® Wipers, manufactured by Kimberly Clark, Neenah, Wis.

Bleach: 4% by weight aqueous solution of calcium hypochlorite.

Sodium thiosulfate: 5% by weight aqueous solution, supplied by Tarijian Labs, Inc., Queens Village, N.Y.

HIV infected Cells: H9/IIIB cells ($10^6$ cells/ml of complete culture medium, RPI in 10% fetal calf serum [FCS]), as described above in Example 6.

A first fresh, dry test swab or towlette is impregnated with a 4.0% by weight aqueous solution of calcium hypochlorite by applying 5 (five) ml. of the calcium hypochlorite solution to the test swab. A second fresh, dry test swab or towelette is impregnated with a 5% by weight aqueous solution of sodium thiosulfate by applying 5 (five) ml. of the sodium thiosulfate solution to the test swab.

A small amount of the HIV infected cells are placed on a stainless steel work surface. The sodium hypochlorite impregnated towlette is then wiped or swabbed, over the HIV infected cells, which should inactivate the virus.

The sodium thiosulfate impregnated towlette is then wiped, or swabbed, over the work surface containing the inactivated virus. The sodium thiosulfate should neutralize any residual calcium hypochlorite left on the work surface, thereby preventing the stainless steel surface from being etched by the residual alkaline calcium hypochlorite solution.

The foregoing description has been given for clearness of understanding only, and no unnecessary limitations should be understood therefrom, as modifications will be obvious to those skilled in the art.

What is claimed is:

1. A method for inactivating HIV infected blood, the method comprising the steps of:
   (a) swabbing a surface containing the HIV infected blood with a first absorbent, fibrous towlette impregnated with an aqueous solution of a deactivator selected from the group consisting of calcium hypochlorite, sodium hypochlorite and mixtures thereof, to inactivate HIV present in such HIV infected blood; and
   (b) thereafter swabbing the surface with a second absorbent, fibrous towlette impregnated with an aqueous solution of sodium thiosulfate to neutralize any residual deactivator present on the surface so as to prevent etching of the surface by the residual deactivator.

2. The method of claim 1 wherein the first and second towlettes are made from materials selected from the group consisting of cotton, synthetic blends, and mixtures thereof, the deactivator is sodium hypochlorite, and wherein the ratio of deactivator volume to first towlette weight is in the range of 1.8 to 15 ml/gm, and the ratio of sodium thiosulfate volume to second towlette weight is in the range of 1.8 to 15 ml/gm.

3. A method for inactivating an anticancer drug selected from the group of anticancer drugs consisting of L-asparaginase, carmustine, doxorubicin, daunorubicin, epirubicin, mitoxantrone, mitomycin-C, melphalan, cyclophosphamide, ifosphamide, thio-TEPA, decarbazine, cisplatin, carboplatin, vincristine, vinblastine, vindesine, actinomycin D, bleomycin, etoposide, teniposide, α-interferon, interleukin 2, tumor necrosis factor, G-CSF, and GM-CSF, the method comprising the steps of:
   (a) swabbing a surface containing the anticancer drug with a first absorbent, fibrous towlette impregnated with an aqueous solution of a deactivator selected from the group consisting of calcium hypochlorite, sodium hypochlorite and mixtures thereof, to inactivate the anticancer drug; and
   (b) thereafter swabbing the surface with a second absorbent, fibrous towlette impregnated with an aqueous solution of sodium thiosulfate to neutralize any residual deactivator present on the surface so as to prevent etching of the surface by the residual deactivator.

4. The method of claim 3 wherein the first and second towlettes are made from materials selected from the group consisting of cotton, synthetic blends, and mixtures thereof, the deactivator is sodium hypochlorite, and wherein the ratio of deactivator volume to first towlette weight is in the range of 1.8 to 15 ml/gm, and the ratio of sodium thiosulfate volume to second towlette weight is in the range of 1.8 to 15 ml/gm.

* * * * *